US00PP15054P2

(12) United States Plant Patent
Leue

(10) Patent No.: US PP15,054 P2
(45) Date of Patent: Jul. 27, 2004

(54) HIBISCUS PLANT 'BALHIBLU'

(50) Latin Name: *Hibiscus moscheutos*
Varietal Denomination: Balhiblu

(75) Inventor: Ellen Leue, DeKalb, IL (US)

(73) Assignee: Ball Horticultural, Inc., West Chicago, IL (US)

( * ) Notice: Subject to any disclaimer, the term of this patent is extended or adjusted under 35 U.S.C. 154(b) by 8 days.

(21) Appl. No.: 10/627,422

(22) Filed: Jul. 25, 2003

(51) Int. Cl.[7] ..... A01H 5/00
(52) U.S. Cl. ..... Plt./257
(58) Field of Search ..... Plt./257

*Primary Examiner*—Anne Marie Grunberg
*Assistant Examiner*—Susan B. McCormick-Ewoldt
(74) *Attorney, Agent, or Firm*—Wood, Phillips, Katz, Clark & Mortimer

(57) ABSTRACT

A new and distinct cultivar of *Hibiscus moscheutos* plant named 'Balhiblu', characterized by its upright and uniform plant habit, flowers having light pink edge fading towards the center to white with a dark red "eye", and light green-colored leaves.

1 Drawing Sheet

Latin name of the genus and species of the plant claimed: *Hibiscus moscheutos.*
Variety denomination: 'Balhiblu'.

BACKGROUND OF THE INVENTION

The present invention relates to a new and distinct cultivar of Hibiscus, botanically known as *Hibiscus moscheutos*, hereinafter referred to by the name 'Balhiblu'.

The new Hibiscus is a product of a planned breeding program conducted by the inventor in Elburn, Ill. The objective of the breeding program was to create new well-branched Hibiscus cultivars with desirable flower color, and uniform and compact plant habit appropriate for container production.

The new Hibiscus originated from a cross made by the inventor in Elburn, Ill. in 2000, of the *Hibiscus moscheutos* proprietary breeding line 102-5-1 (not patented), as the female, or seed, parent with the *Hibiscus moscheutos* proprietary breeding line 116-23-3 (not patented), as the male, or pollen, parent. The female parent, *Hibiscus moscheutos* proprietary breeding line 102-5-1, has a very good habit is floriferous with flowers having a white "eye". The male parent, *Hibiscus moscheutos* proprietary breeding line 116-23-3 has medium height is fairly floriferous with a good habit and very deep pink flowers.

Compared to plants of the female parent, *Hibiscus moscheutos* proprietary breeding line 102-5-1, the flowers of the cultivar 'Balhiblu' have a dark red "eye", whereas the flowers of the female parent have a white "eye". The cultivar 'Balhiblu' is better branched, and more free flowering than the female parent.

Compared to plants of male parent, *Hibiscus moscheutos* proprietary breeding line 116-23-3, flowers of the cultivar 'Balhiblu' have a light pink edge fading towards the center to white with a dark red "eye" while the male parent has deep pink flowers. The cultivar 'Balhiblu' is more vigorous and more free flowering, with larger flowers than the male parent.

The cultivar 'Balhiblu' was discovered and selected by the Inventor as a flowering plant within the progeny of the stated cross in a controlled environment in Elburn, Ill., on Aug. 7, 2001. The cultivar 'Balhiblu' is perennial to Zone 5.

Both parents have a degree of homozygosity such that the progeny of the cross 102-5-1 times 116-23-3 are phenotypically uniform and essentially identical to 'Balhiblu'. Removal of the terminal apex will improve branching in asexually reproduced plants. Accordingly, plants that are phenotypically identical to 'Balhiblu' can be produced by sexual reproduction as well as asexual reproduction.

Asexual reproduction of the new Hibiscus by vegetative terminal cuttings taken in a controlled environment in Santa Paula, Calif. has shown that the unique features of this new Hibiscus are stable and reproduced true to type in successive generations.

SUMMARY OF THE INVENTION

The following traits have been repeatedly observed and are determined to be the unique characteristics of 'Balhiblu'. These characteristics in combination distinguish 'Balhiblu' as a new and distinct cultivar:

1. Compact, upright, and symmetrical plant habit that is suitable for container production;
2. Early to flower;
3. Bushy, well branched;
4. Large flowered and floriferous; and
5. Flowers have a light pink edge fading towards the center to white with a dark red "eye".

Plants of the new Hibiscus 'Balhiblu' can be compared to plants of the Hibiscus Disco Belle Series Pink (not patented), commercially available from Sakata Seed, Inc., Morgan Hill, Calif. 95037. In side-by-side comparisons conducted in Santa Paula, Calif., plants of the new Hibiscus 'Balhiblu' differ from plants of Disco Belle Series Pink in the following characteristics:

1. Plants of the new Hibiscus 'Balhiblu' are 20% more compact;
2. Plants of the new Hibiscus 'Balhiblu' are earlier to flower by approximately one week;
3. Plants of the new Hibiscus 'Balhiblu' have more branches;
4. Plants of the new Hibiscus 'Balhiblu' are branched more uniformly; and
5. Plants of the new Hibiscus 'Balhiblu' are more floriferous.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ from the color values cited in the detailed botanical description that accurately describe the colors of the new Hibiscus. The photograph comprises a side perspective view of a single flowering plant of 'Balhiblu' grown in a container.

DETAILED BOTANICAL DESCRIPTION

The cultivar 'Balhiblu' has not been observed under all possible environmental conditions. The phenotype may vary somewhat with variations in environment and cultural practices such as temperature, light intensity, water status and/or fertilizer rate or type without, however, any variance in genotype.

The photographs and following observations, measurements and values describe plants grown in Santa Paula, Calif. with 1 plant per 12.5 cm container in glass-covered greenhouses during the winter and spring under conditions which closely approximate commercial production. During the production of the plants, day temperatures ranged from 18 to 23° C. and night temperatures ranged from 16 and 21° C. Plants and controls were treated with plant growth regulators as follows: one time with Cycocel at 250 ppm, followed by two times with a mixture of B-9 at 2500 ppm and Cycocel at 500 ppm. Plants were approximately 4.5 months old when the photographs and color values were determined. The chart used in the identification of the colors described herein is The R.H.S. Colour Chart of The Royal Horticultural Society, London, England. The color values were determined on Jul. 7, 2003 between 10:00 am and 2:00 pm under natural daylight conditions.

Botanical classification: *Hibiscus moscheutos* cultivar 'Balhiblu'.

Parentage:

*Female or seed parent*.—Proprietary selection of *Hibiscus moscheutos* identified as code number 102-5-1, not patented.

*Male or pollen parent*.—Proprietary selection of *Hibiscus moscheutos* identified as code number 116-23-3, not patented.

Propagation:

*Type*.—By vegetative terminal cuttings.

*Time to initiate roots*.—About 17 days at temperatures of 27–29° C. days and 21 to 22° C. nights.

*Time to develop roots*.—About 26 days at temperatures of 27–29° C. days and 21 to 22° C. nights.

*Root description*.—Thick, fibrous and white in color.

Plant description:

*Plant form and growth habit*.—Upright, lateral branches, vigorous growth habit.

*Branching habit*.—Freely branched, one to six lateral branches.

*Plant height*.—38 cm.

*Plant diameter* (*area of spread*).—30 cm.

*Lateral branch description*.—Length: 27 to 45 cm. Diameter: 6 mm at base to 2 mm at tip. Texture: Immature: Smooth. Texture: Mature: Woody and rough. Color: Immature: 137D. Color: Mature: 139D.

*Foliage description*.—Arrangement: Alternate. Length: 8 cm, from central stem. Width: 6.7 cm. Shape: Ovate. Apex: Acute to narrowly acuminate. Base: Cordate to obtuse. Margin: Entire to sinuate. Aspect: Concave. Texture: Upper surface: Glabrous. Texture: Lower surface: Glabrous. Venation pattern: Palmate. Color: Young foliage, upper surface: 144A. Young foliage, lower surface: 144A. Mature foliage, upper surface: 137B. Mature foliage, lower surface: 138B. Venation, upper surface: 145C. Venation, lower surface: 145C. Petiole: Length: 2 to 3 cm. Diameter: 1 mm. Texture: Upper surface: Glabrous. Texture: Lower surface: Glabrous. Color: 145A.

Flower description:

*Flower arrangement*.—5 or more apical buds, side facing.

*Flower appearance*.—5 rounded petals, flowers have light pink edge fading towards the center to white with a dark red "eye", open about 1 day.

*Natural flowering season*.—Spring and summer.

*Flower diameter*.—14 to 15 cm.

*Flower length* (*height*).—4.5 cm.

*Flower bud* (*just before showing color*).—Rate of opening: Approximately 2 days. Length: 2.2 cm. Diameter: 1.8 cm. Shape: Ovate. Color: 146C.

*Petals*.—Arrangement: 5 overlapping petals, fused at base. Length: 8 cm. Width: 11 cm. Shape: Broad spatulate. Apex: Rounded. Base: Attenuate. Margin: Entire. Texture: Upper surface: Glabrous. Texture: Lower surface: Glabrous. Color: When opening, upper surface: 159B. Venation: 159B. When opening, lower surface: 159B. Venation: 159B. Base: 158C. Fully opened, upper surface: 56C edge fading to 156D towards the center with a central "eye" 60B. Venation: 156D. Fully opened, lower surface: 155D. Venation: 155D. Base: 155D. Throat: 153B.

*Sepals*.—Appearance: 5 sepals fused into a star shaped calyx. Length: 1.8 cm. Width: 1.5 cm. Shape: Deltoid. Apex: Cuspidate. Margin: Entire. Texture: Inner (upper) surface: Glabrous. Texture: Outer (lower) surface: Glabrous. Color: Inner (upper) surface: 137C. Color: Outer (lower) surface: 138B.

*Bracts*.—Appearance: 9 bracts fused at base. Length: 1.2 cm. Width: 2 mm at base to 1 mm at tip. Shape: Acicular. Apex: Acuminate. Margin: Entire. Texture: Upper surface: Puberulent. Texture: Lower surface: Glabrous. Color: Upper surface: 144A. Color: Lower surface: 138A.

*Peduncles*.—Length: From 3 to 4 cm. Diameter: 2 mm. Angle: Upright, about 60 degrees. Strength: Strong. Texture: Puberulent. Color: 146C.

*Reproductive organs*.—Androecium: Stamen number: Numerous, approximately 100. Filament length: Approximately 5 mm. Color: Filament: 155D. Anther shape: Globular. Anther size: Approximately 1 mm by 1 mm. Color: Anther: 155D. Amount of pollen: Abundant. Color: Pollen: Approximately 158B. Gynoecium: Pistil length: 4 cm. Pistil diameter apex: 1 cm. Pistil diameter base: Approximately 4 mm. Style texture: Puberulent. Color: Style: 155D. Stigma appearance: 5 rounded. Stigma diameter: Approximately 2 mm. Color: Stigma: 155A. Color: Ovary: 155D.

*Seed*.—The cultivar Balhibred will set seed when exposed to pollinating insects in an outdoor situation. Size: Approximately 3 mm. Shape: Spherical. Texture: Smooth. Color: Darker than 200A.

Disease resistance: Resistance to common diseases of Hibiscus have not been observed.

What is claimed is:

1. A new and distinct cultivar of *Hibiscus moscheutos* plant named 'Balhiblu', substantially as herein shown and described.

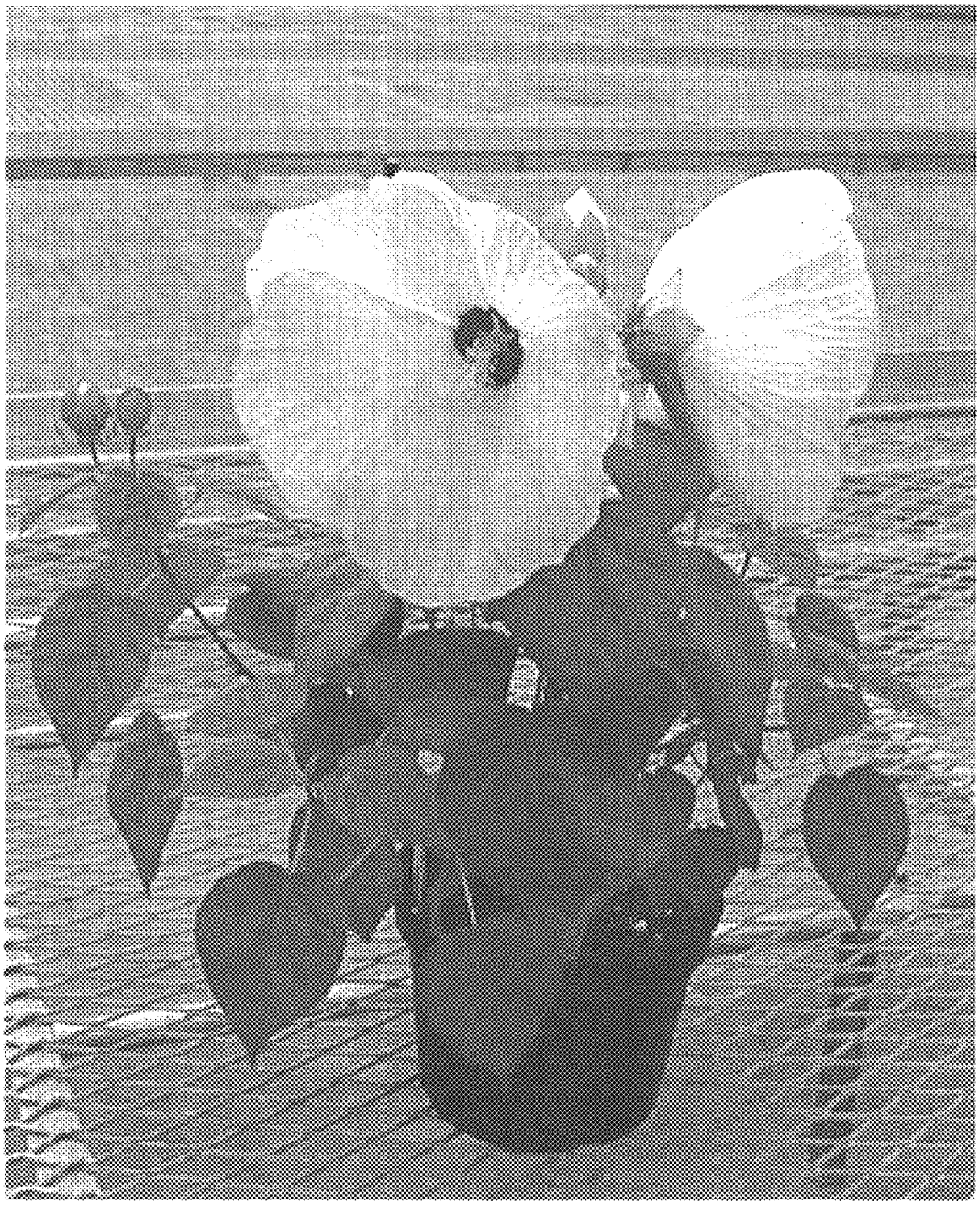

* * * * *